(12) United States Patent
Corson et al.

(10) Patent No.: US 6,929,951 B2
(45) Date of Patent: Aug. 16, 2005

(54) METHOD AND SYSTEM FOR MOLECULAR ARRAY SCANNER CALIBRATION

(75) Inventors: John F. Corson, Stanford, CA (US); Andreas N. Dorsel, Menlo Park, CA (US); Russell A. Parker, San Jose, CA (US); Andre B. Chow, Belmont, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 519 days.

(21) Appl. No.: 10/086,932

(22) Filed: Feb. 28, 2002

(65) Prior Publication Data

US 2003/0165871 A1 Sep. 4, 2003

(51) Int. Cl.⁷ .......................... G01N 31/00; G01N 33/53
(52) U.S. Cl. .............................. 436/8; 436/164; 702/19; 702/27; 702/28; 702/32; 435/6; 435/287.2; 435/7.9
(58) Field of Search ............................ 436/8, 164, 172; 702/19, 22, 27, 28, 32; 422/82.05, 82.08, 82.09; 73/1.01; 435/6, 287.2, 7.9

(56) References Cited

U.S. PATENT DOCUMENTS

| | | |
|---|---|---|
| 5,599,695 A | 2/1997 | Pease et al. |
| 5,721,435 A | 2/1998 | Troll |
| 5,753,788 A | 5/1998 | Fodor et al. |
| 5,763,870 A | 6/1998 | Sadler et al. |
| 6,171,797 B1 | 1/2001 | Perbost |
| 6,180,351 B1 | 1/2001 | Cattell |
| 6,232,072 B1 | 5/2001 | Fisher |
| 6,242,266 B1 | 6/2001 | Schleifer et al. |
| 6,323,043 B1 | 11/2001 | Caren et al. |
| 6,329,143 B1 | 12/2001 | Stryer et al. |
| 6,371,370 B2 | 4/2002 | Sadler et al. |
| 6,403,957 B1 | 6/2002 | Fodor et al. |
| 6,471,916 B1 * | 10/2002 | Noblett .................... 422/82.08 |
| 6,583,424 B2 * | 6/2003 | Staton et al. ............ 250/461.2 |
| 6,794,424 B2 * | 9/2004 | Holcomb et al. ........... 523/137 |
| 2003/0065449 A1 * | 4/2003 | Wolber et al. ................ 702/19 |
| 2003/0143751 A1 * | 7/2003 | Corson ....................... 436/164 |

FOREIGN PATENT DOCUMENTS

| | | | |
|---|---|---|---|
| EP | 1186673 | * | 3/2002 |
| WO | 01/06238 | * | 1/2001 |

* cited by examiner

Primary Examiner—Maureen M. Wallenhorst (57) ABSTRACT

A method and system for calibrating molecular arrays to a reference molecular array, and for subsequently calibrating the molecular arrays to maintain a constant signal-intensity-to-label-concentration ratio. In the first step of the two-step calibration method, a reference array coated with the fluorophore or chromophore used to label probe molecules is employed, while in the second step of the two-step method, a reference array coated with a stable dye is employed.

8 Claims, 11 Drawing Sheets

METHOD AND SYSTEM FOR MOLECULAR ARRAY SCANNER CALIBRATION

TECHNICAL FIELD

The present invention is related to molecular array scanners and, in particular, to a method and system for calibrating molecular array scanners.

BACKGROUND OF THE INVENTION

The present invention is related to acquisition of molecular-array data and other types of genetic, biochemical, and chemical data from molecular arrays by molecular array scanners. A general background of molecular-array technology is first provided, in this section, to facilitate discussion of the scanning techniques described in following sections.

Array technologies have gained prominence in biological research and are likely to become important and widely used diagnostic tools in the healthcare industry. Currently, molecular-array techniques are most often used to determine the concentrations of particular nucleic-acid polymers in complex sample solutions. Molecular-array-based analytical techniques are not, however, restricted to analysis of nucleic acid solutions, but may be employed to analyze complex solutions of any type of molecule that can be optically or radiometrically scanned and that can bind with high specificity to complementary molecules synthesized within, or bound to, discrete features on the surface of an array. Because arrays are widely used for analysis of nucleic acid samples, the following background information on arrays is introduced in the context of analysis of nucleic acid solutions following a brief background of nucleic acid chemistry.

Figure 1:
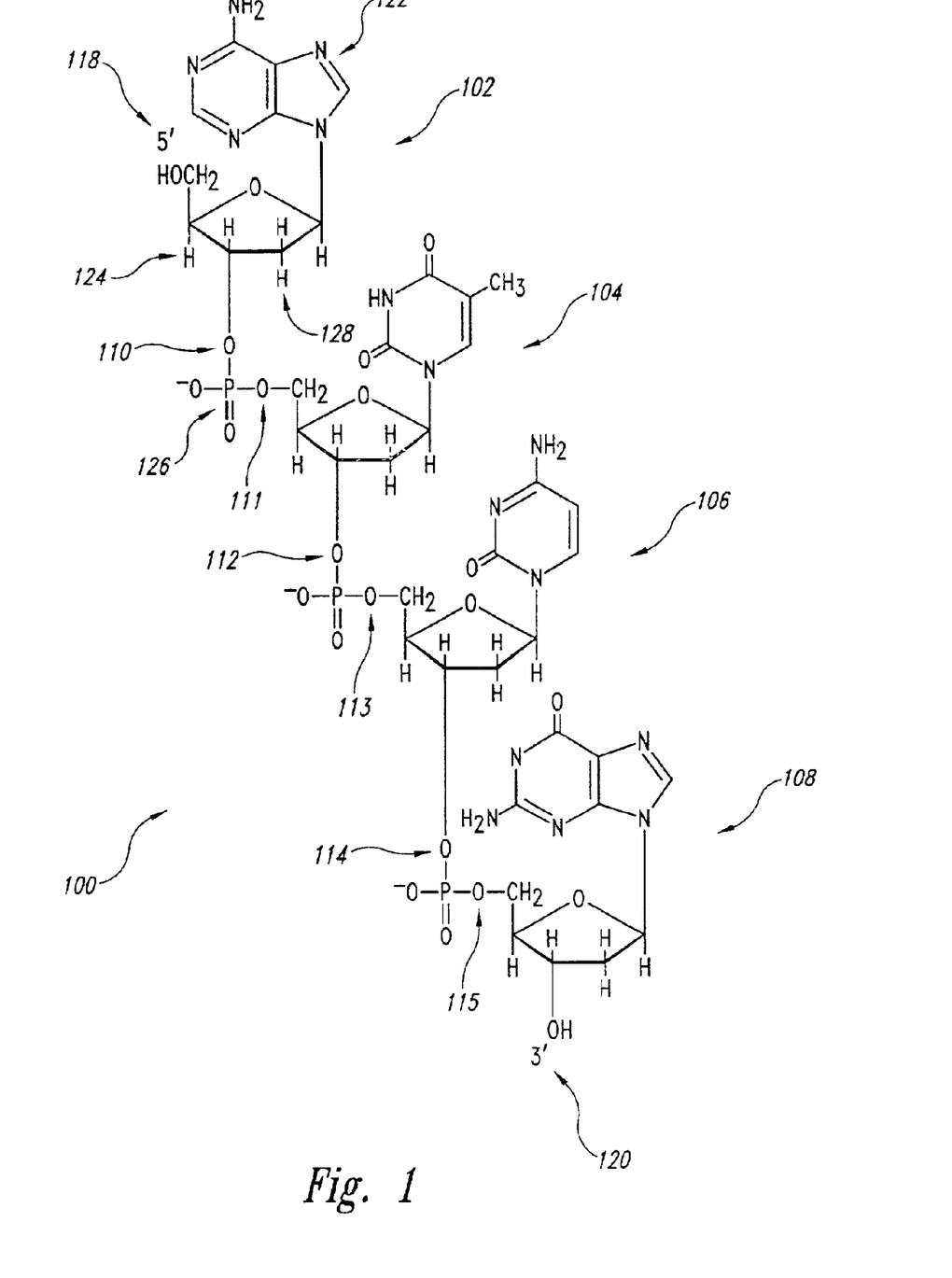
FIG. 1 illustrates a short DNA polymer 100, called an oligomer, composed of the following subunits: (1) deoxyadenosine 102; (2) deoxy-thymidine 104; (3) deoxy-cytosine 106; and (4) deoxy-guanosine 108.

Deoxyribonucleic acid ("DNA") and ribonucleic acid ("RNA") are linear polymers, each synthesized from four different types of subunit molecules. The subunit molecules for DNA include: (1) deoxy-adenosine, abbreviated "A," a purine nucleoside; (2) deoxy-thymidine, abbreviated "T," a pyrimidine nucleoside; (3) deoxy-cytosine, abbreviated "C," a pyrimidine nucleoside; and (4) deoxy-guanosine, abbreviated "G," a purine nucleoside. The subunit molecules for RNA include: (1) adenosine, abbreviated "A," a purine nucleoside; (2) uracil, abbreviated "U," a pyrimidine nucleoside; (3) cytosine, abbreviated "C," a pyrimidine nucleoside; and (4) guanosine, abbreviated "G," a purine nucleoside. FIG. 1 illustrates a short DNA polymer 100, called an oligomer, composed of the following subunits: (1) deoxy-adenosine 102; (2) deoxy-thymidine 104; (3) deoxy-cytosine 106; and (4) deoxy-guanosine 108. When phosphorylated, subunits of DNA and RNA molecules are called "nucleotides" and are linked together through phosphodiester bonds 110–115 to form DNA and RNA polymers. A linear DNA molecule, such as the oligomer shown in FIG. 1, has a 5' end 118 and a 3' end 120. A DNA polymer can be chemically characterized by writing, in sequence from the 5' end to the 3' end, the single letter abbreviations for the nucleotide subunits that together compose the DNA polymer. For example, the oligomer 100 shown in FIG. 1 can be chemically represented as "ATCG." A DNA nucleotide comprises a purine or pyrimidine base (e.g. adenine 122 of the deoxy-adenylate nucleotide 102), a deoxy-ribose sugar (e.g. deoxy-ribose 124 of the deoxy-adenylate nucleotide 102), and a phosphate group (e.g. phosphate 126) that links one nucleotide to another nucleotide in the DNA polymer. In RNA polymers, the nucleotides contain ribose sugars rather than deoxy-ribose sugars. In ribose, a hydroxyl group takes the place of the 2' hydrogen 128 in a DNA nucleotide. RNA polymers contain uridine nucleosides rather than the deoxy-thymidine nucleosides contained in DNA. The pyrimidine base uracil lacks a methyl group (130 in FIG. 1) contained in the pyrimidine base thymine of deoxy-thymidine.

The DNA polymers that contain the organization information for living organisms occur in the nuclei of cells in pairs, forming double-stranded DNA helixes. One polymer of the pair is laid out in a 5' to 3' direction, and the other polymer of the pair is laid out in a 3' to 5' direction. The two DNA polymers in a double-stranded DNA helix are therefore described as being anti-parallel. The two DNA polymers, or strands, within a double-stranded DNA helix are bound to each other through attractive forces including hydrophobic interactions between stacked purine and pyrimidine bases and hydrogen bonding between purine and pyrimidine bases, the attractive forces emphasized by conformational constraints of DNA polymers. Because of a number of chemical and topographic constraints, double-stranded DNA helices are most stable when deoxy-adenylate subunits of one strand hydrogen bond to deoxy-thymidylate subunits of the other strand, and deoxy-guanylate subunits of one strand hydrogen bond to corresponding deoxy-cytidilate subunits of the other strand.

Figure 2A:
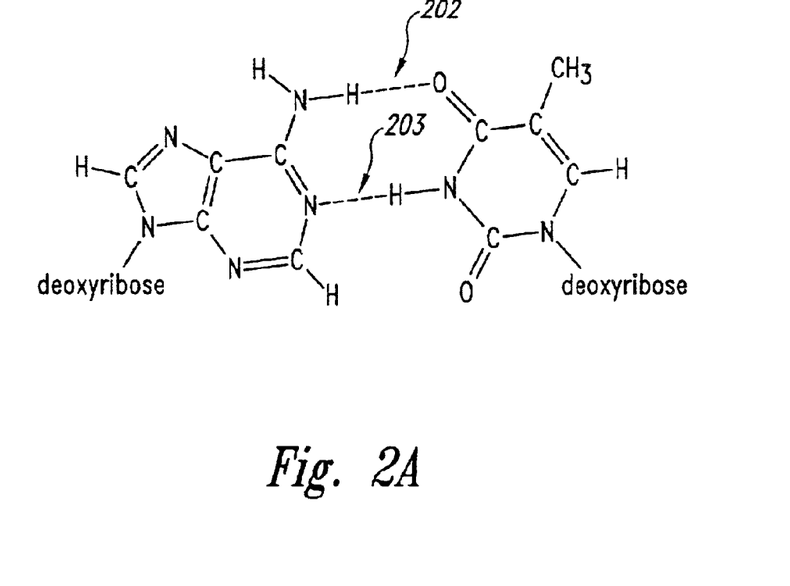
FIGS. 2A–B illustrate the hydrogen bonding between the purine and pyrimidine bases of two anti-parallel DNA strands.
Figure 2B:
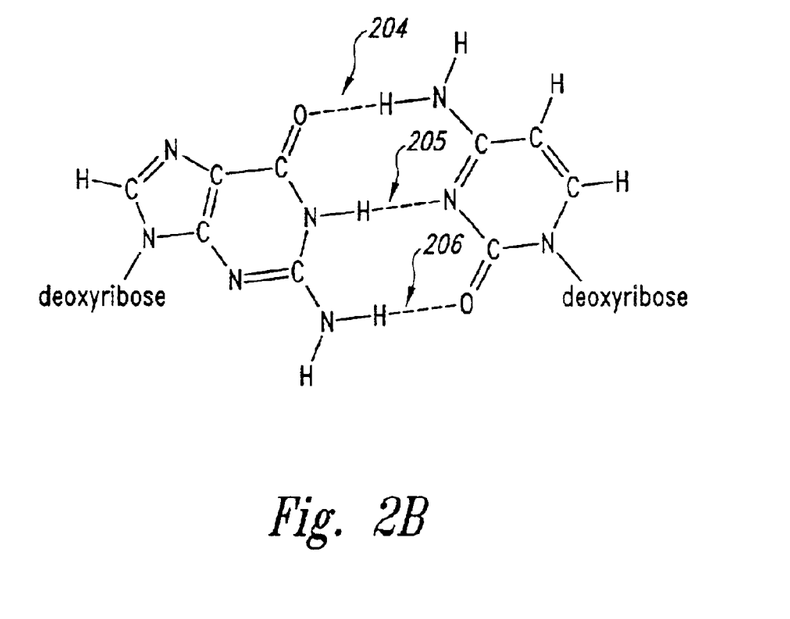

FIGS. 2A–B illustrate the hydrogen bonding between the purine and pyrimidine bases of two anti-parallel DNA strands. FIG. 2A shows hydrogen bonding between adenine and thymine bases of corresponding adenosine and thymidine subunits, and FIG. 2B shows hydrogen bonding between guanine and cytosine bases of corresponding guanosine and cytosine subunits. Note that there are two hydrogen bonds 202 and 203 in the adenine/thymine base pair, and three hydrogen bonds 204–206 in the guanosine/cytosine base pair, as a result of which GC base pairs contribute greater thermodynamic stability to DNA duplexes than AT base pairs. AT and GC base pairs, illustrated in FIGS. 2A–B, are known as Watson-Crick ("WC") base pairs.

Figure 3:
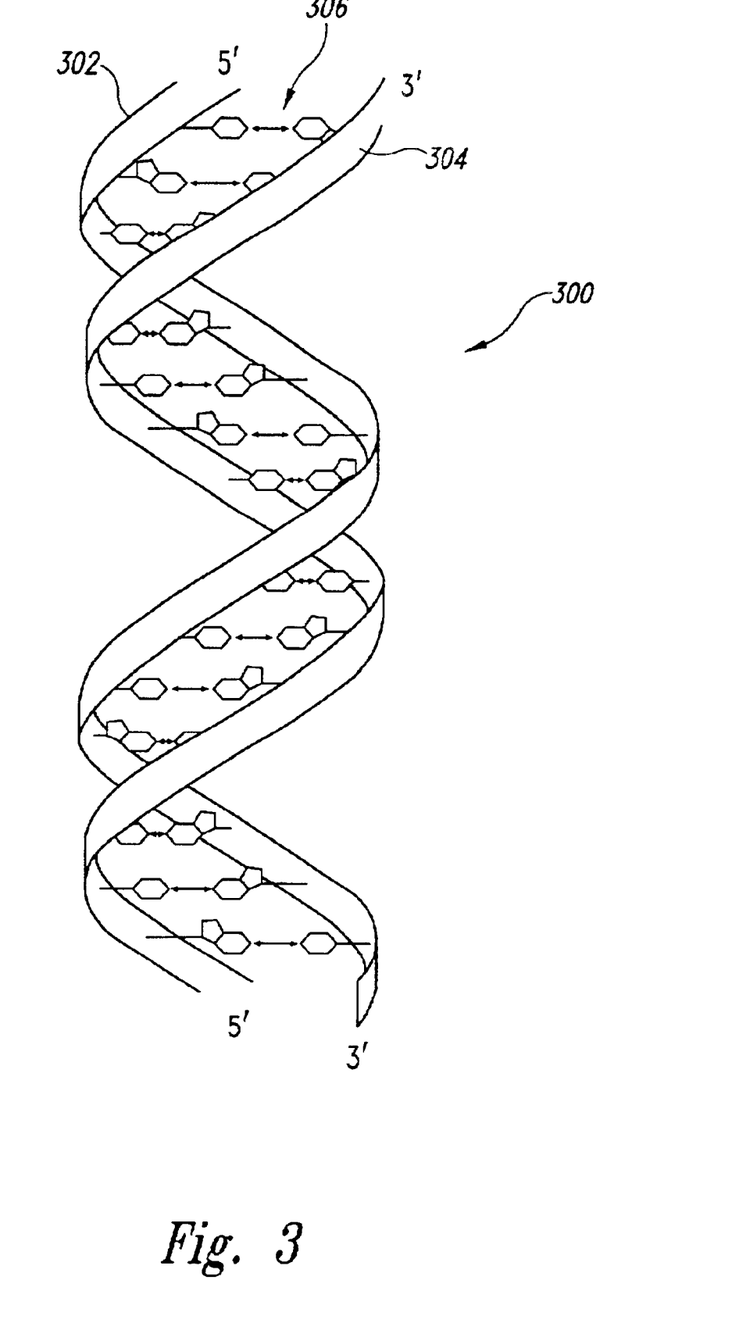
FIG. 3 illustrates a short section of a DNA double helix 300 comprising a first strand 302 and a second, anti-parallel strand 304.

Two DNA strands linked together by hydrogen bonds forms the familiar helix structure of a double-stranded DNA helix. FIG. 3 illustrates a short section of a DNA double helix 300 comprising a first strand 302 and a second, antiparallel strand 304. The ribbon-like strands in FIG. 3 represent the deoxy-ribose and phosphate backbones of the two anti-parallel strands, with hydrogen-bonding purine and pyrimidine base pairs, such as base pair 306, interconnecting the two strands. Deoxy-guanylate subunits of one strand are generally paired with deoxy-cytidilate subunits from the other strand, and deoxy-thymidilate subunits in one strand are generally paired with deoxy-adenylate subunits from the other strand. However, non-WC base pairings may occur within double-stranded DNA.

Double-stranded DNA may be denatured, or converted into single stranded DNA, by changing the ionic strength of the solution containing the double-stranded DNA or by raising the temperature of the solution. Single-stranded DNA polymers may be renatured, or converted back into DNA duplexes, by reversing the denaturing conditions, for example by lowering the temperature of the solution containing complementary single-stranded DNA polymers. During renaturing or hybridization, complementary bases of anti-parallel DNA strands form WC base pairs in a cooperative fashion, leading to reannealing of the DNA duplex. Strictly A-T and G-C complementarity between anti-parallel polymers leads to the greatest thermodynamic stability, but partial complementarity including non-WC base pairing may also occur to produce relatively stable associations between partially-complementary polymers. In general, the longer the regions of consecutive WC base pairing between two nucleic acid polymers, the greater the stability of hybridization between the two polymers under renaturing conditions.

Figure 4:
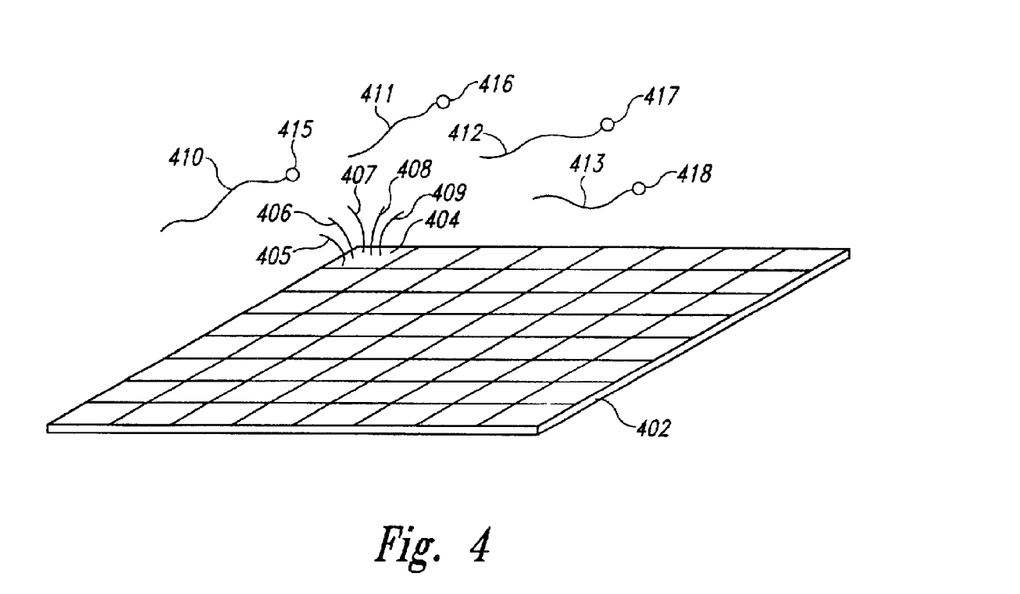
FIGS. 4–7 illustrate the principle of the array-based hybridization assay.
Figure 5:
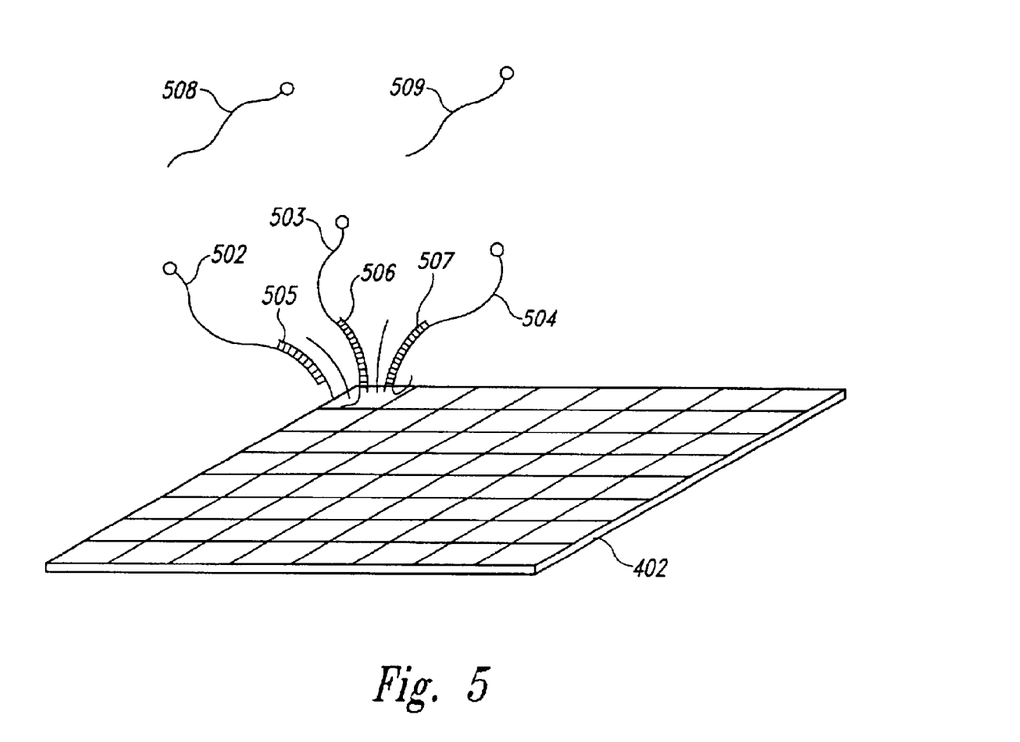
Figure 6:
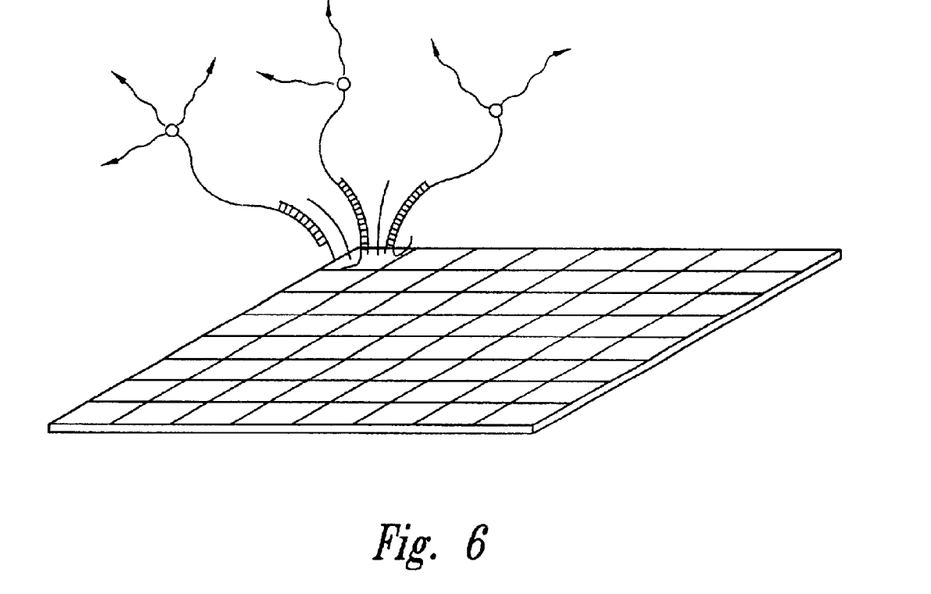

The ability to denature and renature double-stranded DNA has led to the development of many extremely powerful and discriminating assay technologies for identifying the presence of DNA and RNA polymers having particular base sequences or containing particular base subsequences within complex mixtures of different nucleic acid polymers, other biopolymers, and inorganic and organic chemical compounds. One such methodology is the array-based hybridization assay. FIGS. 4–7 illustrate the principle of the array-based hybridization assay. An array (402 in FIG. 4) comprises a substrate upon which a regular pattern of features are prepared by various manufacturing processes. The array 402 in FIG. 4, and in subsequent FIGS. 5–7, has a grid-like two-dimensional pattern of square features, such as feature 404 shown in the upper left-hand corner of the array. It should be noted that many molecular arrays contain disk-shaped features, rather than round features. Each feature of the array contains a large number of identical oligonucleotides covalently bound to the surface of the feature. These bound oligonucleotides are known as probes. In general, chemically distinct probes are bound to the different features of an array, so that each feature corresponds to a particular nucleotide sequence. In FIGS. 4–6, the principle of array-based hybridization assays is illustrated with respect to the single feature 404 to which a number of identical probes 405–409 are bound. In practice, each feature of the array contains a high density of such probes but, for the sake of clarity, only a subset of these are shown in FIGS. 4–6.

Figure 7:
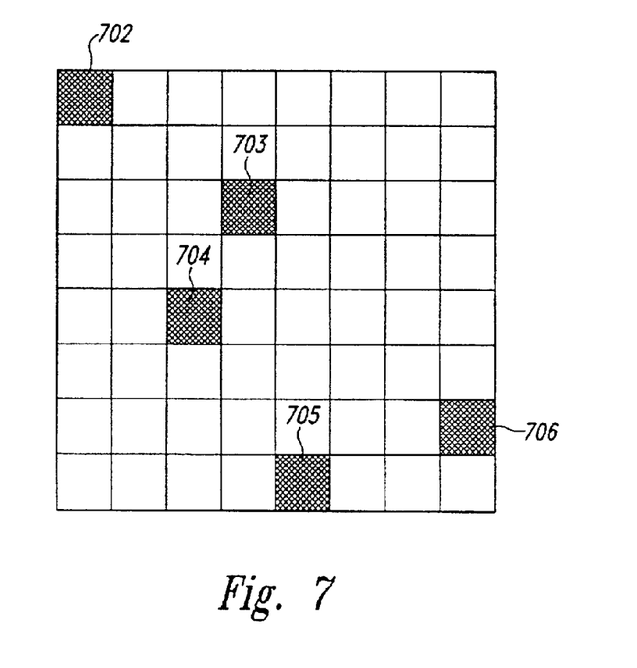

Once an array has been prepared, the array may be exposed to a sample solution of target DNA or RNA molecules (410–413 in FIG. 4) labeled with fluorophores, chemiluminescent compounds, or radioactive atoms 415–418. Labeled target DNA or RNA hybridizes through base pairing interactions to the complementary probe DNA, synthesized on the surface of the array. FIG. 5 shows a number of such target molecules 502–504 hybridized to complementary probes 505–507, which are in turn bound to the surface of the array 402. Targets, such as labeled DNA molecules 508 and 509, that do not contains nucleotide sequences complementary to any of the probes bound to array surface, do not hybridize to generate stable duplexes and, as a result, tend to remain in solution. The sample solution is then rinsed from the surface of the array, washing away any unbound labeled DNA molecules. Finally, the bound labeled DNA molecules are detected via optical or radiometric scanning. FIG. 6 shows labeled target molecules emitting detectable fluorescence, radiation, or other detectable signal. Optical scanning involves exciting labels of bound labeled DNA molecules with electromagnetic radiation of appropriate frequency and detecting fluorescent emissions from the labels, or detecting light emitted from chemiluminescent labels. When radioisotope labels are employed, radiometric scanning can be used to detect the signal emitted from the hybridized features. Additional types of signals are also possible, including electrical signals generated by electrical properties of bound target molecules, magnetic properties of bound target molecules, and other such physical properties of bound target molecules that can produce a detectable signal. Optical, radiometric, or other types of scanning produce an analog or digital representation of the array as shown in FIG. 7, with features to which labeled target molecules are hybridized similar to 706 optically or digitally differentiated from those features to which no labeled DNA molecules are bound. In other words, the analog or digital representation of a scanned array displays positive signals for features to which labeled DNA molecules are hybridized and displays negative features to which no, or an undetectably small number of, labeled DNA molecules are bound. Features displaying positive signals in the analog or digital representation indicate the presence of DNA molecules with complementary nucleotide sequences in the original sample solution. Moreover, the signal intensity produced by a feature is generally related to the amount of labeled DNA bound to the feature, in turn related to the concentration, in the sample to which the array was exposed, of labeled DNA complementary to the oligonucleotide within the feature.

Array-based hybridization techniques allow extremely complex solutions of DNA molecules to be analyzed in a single experiment. An array may contain from hundreds to tens of thousands of different oligonucleotide probes, allowing for the detection of a subset of complementary sequences from a complex pool of different target DNA or RNA polymers. In order to perform different sets of hybridization analyses, arrays containing different sets of bound oligonucleotides are manufactured by any of a number of complex manufacturing techniques. These techniques generally involve synthesizing the oligonucleotides within corresponding features of the array through a series of complex iterative synthetic steps, or depositing oligonucleotides isolated from biological material.

As pointed out above, array-based assays can involve other types of biopolymers, synthetic polymers, and other types of chemical entities. For example, one might attach protein antibodies to features of the array that would bind to soluble labeled antigens in a sample solution. Many other types of chemical assays may be facilitated by array technologies. For example, polysaccharides, glycoproteins, synthetic copolymers, including block copolymers, biopolymer-like polymers with synthetic or derivitized monomers or monomer linkages, and many other types of chemical or biochemical entities may serve as probe and target molecules for array-based analysis. A fundamental principle upon which arrays are based is that of specific recognition, by probe molecules affixed to the array, of target molecules, whether by sequence-mediated binding affinities, binding affinities based on conformational or topological properties of probe and target molecules, or binding affinities based on spatial distribution of electrical charge on the surfaces of target and probe molecules.

An "array", unless a contrary intention appears, includes any one, two or three dimensional arrangement of addressable regions bearing a particular chemical moiety to moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" refers collectively to one or more characteristics of the features, such as feature positioning, one or more feature dimensions, and the chemical moiety or mixture of moieties at a given feature. "Hybridizing" and "binding", with respect to polynucleotides, are used interchangeably.

Any given substrate may carry one, two, four or more or more arrays disposed on a front surface of the substrate. Depending upon the use, any or all of the arrays may be the same or different from one another and each may contain multiple spots or features. A typical array may contain more than ten, more than one hundred, more than one thousand more ten thousand features, or even more than one hundred thousand features, in an area of less than 20 cm$^2$ or even less than 10 cm$^2$. For example, features may have widths (that is, diameter, for a round spot) in the range from a 10 $\mu$m to 1.0 cm. In other embodiments each feature may have a width in the range of 1.0 $\mu$m to 1.0 mm, usually 5.0 $\mu$m to 500 $\mu$m, and more usually 10 $\mu$m to 200 $\mu$m. Non-round features may have area ranges equivalent to that of circular features with the foregoing width (diameter) ranges. At least some, or all, of the features may be of different compositions (for example, when any repeats of each feature composition are excluded the remaining features may account for at least 5%, 10%, or 20% of the total number of features). Interfeature areas will typically (but not essentially) be present which do not carry any polynucleotide (or other biopolymer of a type of which the features are composed). Such interfeature areas typically will be present where the arrays are formed by processes involving drop deposition of reagents but may not be present when, for example, photolithographic array fabrication processes are used. It will be appreciated though, that the interfeature areas, when present, could be of various sizes and configurations.

The array features can have widths (that is, diameter, for a round spot) in the range from a minimum of about 10 $\mu$m to a maximum of about 1.0 cm. In embodiments where very small spot sizes or feature sizes are desired, material can be deposited according to the invention in small spots whose width is in the range about 1.0 $\mu$m to 1.0 mm, usually about 5.0 $\mu$m to 500 $\mu$m, and more usually about 10 $\mu$m to 200 $\mu$m. Features which are not round may have areas equivalent to the area ranges of round features 16 resulting from the foregoing diameter ranges.

Each array may cover an area of less than 100 cm$^2$, or even less than 50, 10 or 1 cm$^2$. In many embodiments, the substrate carrying the one or more arrays will be shaped generally as a rectangular solid (although other shapes are possible), having a length of more than 4 mm and less than 1 m, usually more than 4 mm and less than 600 mm, more usually less than 400 mm; a width of more than 4 mm and less than 1 m, usually less than 500 mm and more usually less than 400 mm; and a thickness of more than 0.01 mm and less than 5.0 mm, usually more than 0.1 mm and less than 2 mm and more usually more than 0.2 and less than 1 mm. With arrays that are read by detecting fluorescence, the substrate may be of a material that emits low fluorescence upon illumination with the excitation light. Additionally in this situation, the substrate may be relatively transparent to reduce the absorption of the incident illuminating laser light and subsequent heating if the focused laser beam travels too slowly over a region. For example, substrate 10 may transmit at least 20%, or 50% (or even at least 70%, 90%, or 95%), of the illuminating light incident on the front as may be measured across the entire integrated spectrum of such illuminating light or alternatively at 532 nm or 633 nm.

Once the labeled target molecule has been hybridized to the probe on the surface, the array may be scanned by an appropriate technique, such as by optical scanning in cases where the labeling molecule is a fluorophore or by radiometric scanning in cases where the signal is generated through a radioactive decay of labeled target. In the case of optical scanning, more than one fluorophore can be excited, with each different wavelength at which an array is scanned producing a different signal. In optical scanning, it is common to describe the signals produced by scanning in terms of the colors of the wavelengths of light employed for the scan. For example, a red signal is produced by scanning the array with light having a wavelength corresponding to that of visible red light.

Scanning of a feature by an optical scanning device or radiometric scanning device generally produces a scanned image comprising a rectilinear grid of pixels, with each pixel having a corresponding signal intensity. These signal intensities are processed by an array-data-processing program that analyzes data scanned from an array to produce experimental or diagnostic results which are stored in a computer-readable medium, transferred to an intercommunicating entity via electronic signals, printed in a human-readable format, or otherwise made available for further use. Molecular array experiments can indicate precise gene-expression responses of organisms to drugs, other chemical and biological substances, environmental factors, and other effects. Molecular array experiments can also be used to diagnose disease, for gene sequencing, and for analytical chemistry. Processing of molecular array data can produce detailed chemical and biological analyses, disease diagnoses, and other information that can be stored in a computer-readable medium, transferred to an intercommunicating entity via electronic signals, printed in a human-readable format, or otherwise made available for further use.

Figure 8:
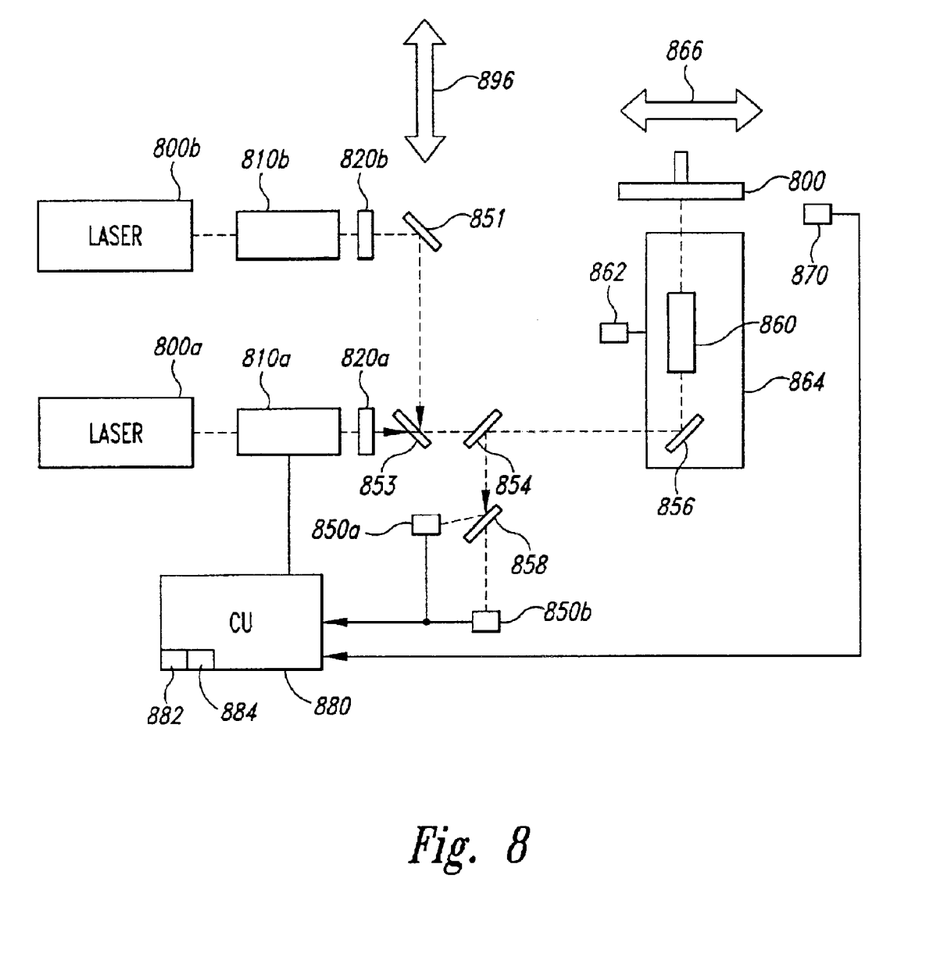
FIG. 8 is a block diagram of major optical and electronic components of a molecular array scanner.

FIG. 8 illustrates components of a molecular array scanner. Lasers 800*a–b* emit coherent light that passes through electro-optic modulators ("EOMs") 810*a–b* with attached polarizers 820*a–b*. Each EOM and corresponding polarizer together act as a variable optical attenuator. A control signal in the form of a variable voltage is applied to each EOM 810*a–b* by controller 880. The controller 880 may include a suitably programmed processor, logic circuit, firmware, or a combination of software programs, logic circuits, and firmware. The control signal changes the polarization of the laser light, which alters the intensity of the light that passes through the EOM. In general, laser 800*a* provides coherent light of a different wavelength than that provided by laser 810*b*. For example, one laser may provide red light and the other laser may provide green light. The beams may be combined along a path toward a stage 800 by the use of full mirror 851 and dichroic mirror 853. The light from the lasers 800*a–b* is then transmitted through a dichroic beam splitter 854, reflected off fully reflecting mirror 856, and then focused, using optical components in beam focuser 860, onto a molecular array mounted on a holder 800. Fluorescent light, emitted at two different wavelengths (for example, green light and red light) from features of the molecular array in response to illumination by the laser light, is imaged using the optics in the focuser/scanner 860, and is reflected off mirrors 856 and 854. The two different wavelengths are further separated by a dichroic mirror 858 and are passed to photodetectors 850*a–b*. More optical components (not shown in FIG. 8) may be used between the dichroic mirror and the photodetectors 850*a–b*, such as lenses, pinholes, filters, and fibers. The photodetectors 850*a–b* may be of various different types, including photo-multiplier tubes, charge-coupled devices, and avalanche photodiodes.

A scan system causes a light spot from each laser 800*a–b* to be moved in a regular pattern about the surface of the molecular array. The molecular array is mounted to a stage that can be moved in horizontal and vertical directions to position light from the lasers onto a particular region at the surface of the molecular array, from which region fluorescent emission is passed back to the photodetectors via the optical path described above. An autofocus detector 870 is provided to sense and correct any offset between different regions of the molecular array and the focal plane of the system during scanning. An autofocus system includes detector 870, processor 880, and a motorized adjuster to move the stage in the direction of arrow 896.

The controller 880 receives signals from photodetectors 850*a–b*, called "channels," corresponding to the intensity of the green and red fluorescent light emitted by probe labels excited by the laser light. The controller 880 also receives a signal from autofocus offset detector 870 in order to control stage adjustment, provides the control signal to the EOMs 810*a–b*, and controls the scan system. Controller 880 may also analyze, store, and output data relating to emitted signals received from detectors 850*a–b*.

Pixel-based signal intensities produced by molecular array scanners often correspond to absolute concentrations of mRNA molecules or other chemical, biological, or pharmaceutical compounds in sample solutions. It is important therefore that the pixel-based signal intensities produced by different molecular array scanners for a given number of fluorophores or chromophores within a region of the surface of a molecular array be identical. Thus, molecular array scanners must be calibrated to a common standard. Unfortunately, methods for precisely calibrating molecular arrays have been elusive. Designers, manufacturers, and users of molecular array scanners have thus recognized a need for a method for precisely calibrating molecular array scanners to a common standard.

SUMMARY OF THE INVENTION

One embodiment of the present invention provides a two-step molecular array calibration method for calibrating molecular arrays to a reference molecular array, and for subsequently calibrating the molecular arrays to maintain a constant signal-intensity-to-label-concentration ratio. In the first step of the two-step calibration method, a reference array coated with the fluorophore or chromophore used to label probe molecules is employed, while in the second step of the two-step method, a reference array coated with a stable dye is employed.

DETAILED DESCRIPTION OF THE INVENTION

One embodiment of the present invention provides a means for calibrating molecular array scanners to a reference molecular array scanner and subsequently calibrating the molecular array scanners to maintain the initial calibration. This two-step calibration method uses a first reference array coated with the same dye that is subsequently used in probe molecules and scanned by the molecular arrays during data collection and uses as a second reference array coated with a more stable dye that does not degrade significantly over repeated scans.

Figure 9:
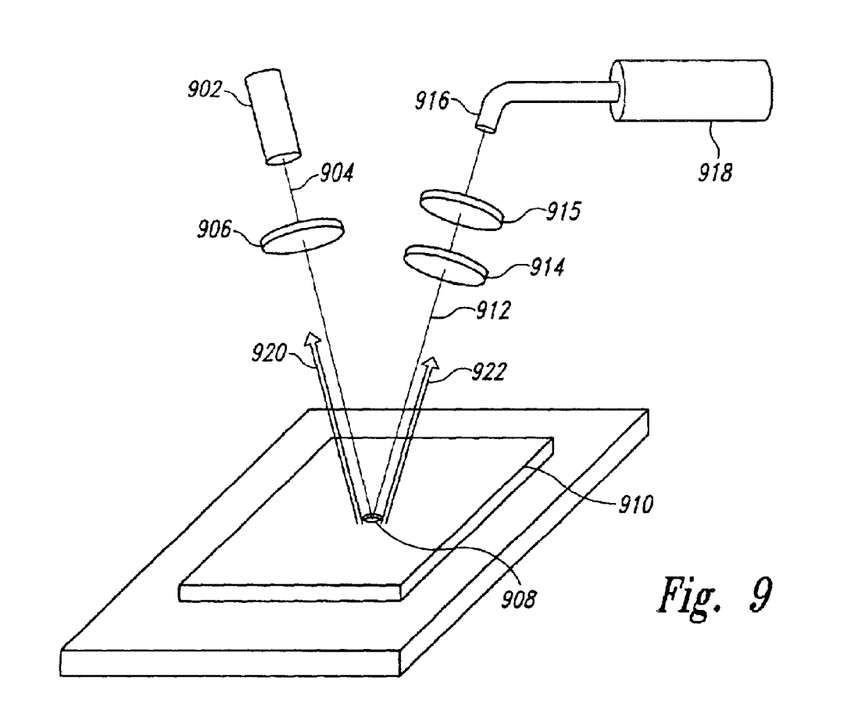
FIG. 9 shows an abstract representation of the excitation and emission-detection components of a molecular array scanner.

FIG. 9 shows an abstract representation of the excitation and emission-detection components of a molecular array scanner. In FIG. 9, a laser source 902 generates a coherent light beam of a particular wavelength 904 that may be optically filtered and focused by filtering and focusing components 906 to impinge on a small region 908 of the surface of a molecular array 910. Excited target molecules hybridized to the surface of the molecular array are excited by the impinging laser light and subsequently emit fluorescent light, generally at a lower wavelength. The emitted light 912 is focused and filtered by various focusing and filtering components 914–915 to impinge on an optical fiber 916, or another type of light collection material, and input into a photodetector 918 to generate an electronic signal proportional to the intensity of the emitted light falling onto the optical fiber 916. Although it may be possible to include electronic and optical feedback mechanisms, represented in FIG. 9 by arrows 920 and 922, to ensure steady and constant laser illumination intensity at the surface of the molecular array and a steady output voltage following conversion of the current signal output from the photodetector for a known emitted light energy level of a particular wavelength. However, molecular array scanners do not contain a calibration mechanism for correlating the intensity of the laser light to the intensity of the emitted light from the surface of the molecular array. Correlation between the signal produced by the photodetector and the light energy generated by the laser involves many different components of the molecular array scanner and a molecular array being scanned. For example, differences in the filtering and optical components in different molecular array scanners may cause differences in the signals generated by the molecular array scanners with respect to constant laser-light intensity. As another example, differences in the surface characteristics of a molecular array, including differences in the chemical environment of fluorophores or chromophores employed to label probe molecules, can result in variations in the signal generated for a given laser-light intensity. In general, the relationship between laser-light intensity and the electronic signal corresponding to emitted-light intensity from probe labels must be determined by a calibration method for each molecular array scanner. Molecular array scanners of a particular type also need to be calibrated amongst themselves, so that scanning of a standard reference array generates the same electronic output signal in every molecular array scanner of the particular type.

Figure 10:
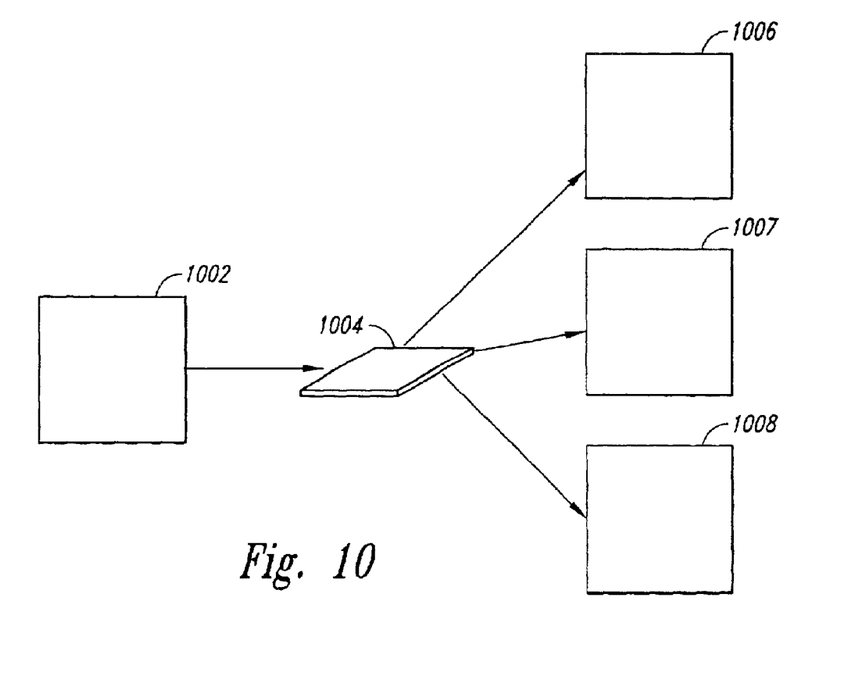
FIG. 10 illustrates the current approach to molecular array-scanner calibration.

FIG. 10 illustrates a current approach to molecular array-scanner calibration. A reference molecular array scanner 1002 is calibrated using a reference array 1004. Thus, while scanning the reference array, the reference molecular array scanner 1002 is internally calibrated to produce a known output electronic signal for a known laser-light intensity averaged for all positions on the surface of the reference array 1004. The reference array 1004 is then used to calibrate other molecular array scanners 1006–1008. Each scanner scans the reference array 1004, and each molecular array scanner 1006–1008 is adjusted to produce electronic signal intensities equal to the averaged electronic signal intensity produced by the reference molecular array scanner 1002. Two different types of reference arrays 1004 may be employed. One type of reference array, referred to as a "same-dye reference array," is coated with the same dye that is used to label probe molecules for actual molecular array experiments. Another type of reference array, referred to as a "stable-dye reference array," uses a different dye than the dye used to label probe molecules, but that has more stable fluorescence-emission characteristics over repeated scans. Unfortunately, the calibration method illustrated in FIG. 10 is flawed, regardless of whether a same-dye reference array or a stable-dye reference array is used.

Figure 11A:
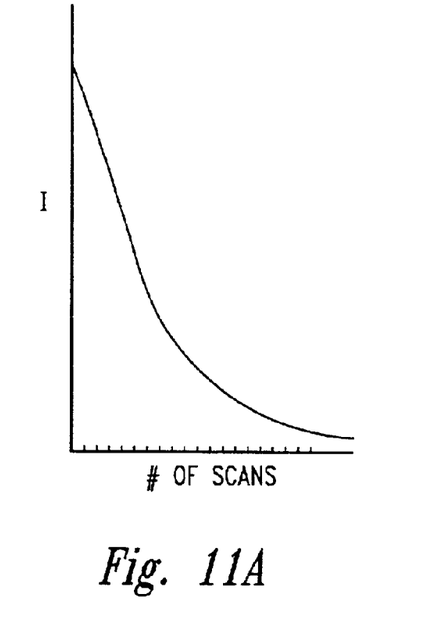
FIGS. 11A–B illustrate dye and scanner properties that inhibit precise calibration using same-dye and stable-dye reference arrays.
Figure 11B:
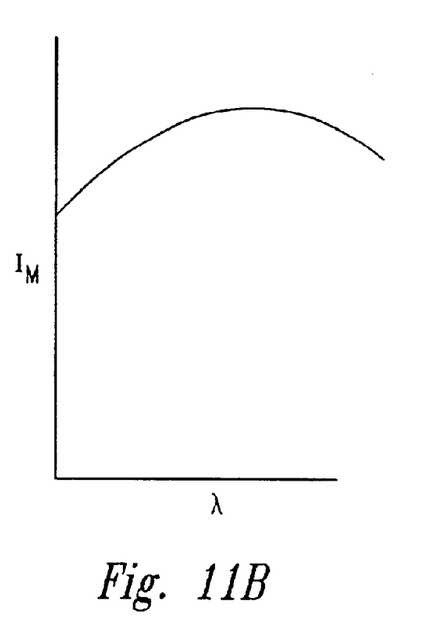

FIGS. 11A–B illustrate dye and scanner properties that inhibit precise calibration using same-dye and stable-dye reference arrays. It should be noted that the relationships graphed in FIGS. 11A–B, and FIGS. 12, 13, 15, and 16 are hypothetical relationships, employed to illustrate general characteristics of molecular array scanners, rather than experimentally derived data from a particular molecular array scanner or molecular array scanners. In FIG. 11A, a function between electronic signal intensity I, plotted on the vertical axis, generated by a same-dye reference array with respect to the number of scans carried out on the same-dye reference array, plotted along the horizontal axis, is plotted. Many of the fluorophores and chromophores used to label probe molecules are chemically unstable with respect to laser-light illumination. Thus, as shown in FIG. 11A, the intensity of the signal generated from scanning a same-dye reference array decreases with each scan of the same-dye reference array. FIG. 11B shows a functional relationship between the intensity of the electronic signal generated for a constant amount of excitation light with respect to the wavelength of the emitted light. In FIG. 11B, the intensity of the generated electronic signal is plotted along the vertical axis, and the wavelength of the emitted light is plotted along the horizontal axis. Thus, as with any electro-optical detection system, the signal generated for a constant amount of excitation light may vary with the wavelength of the emitted light, due to wavelength-dependent absorption characteristics of filters and optics, spectral response of photodetectors, and other such phenomenon. The overall spectral response of one molecular array scanner may differ from that of another, because of wavelength-dependent characteristics that vary from scanner to scanner.

Figure 12:
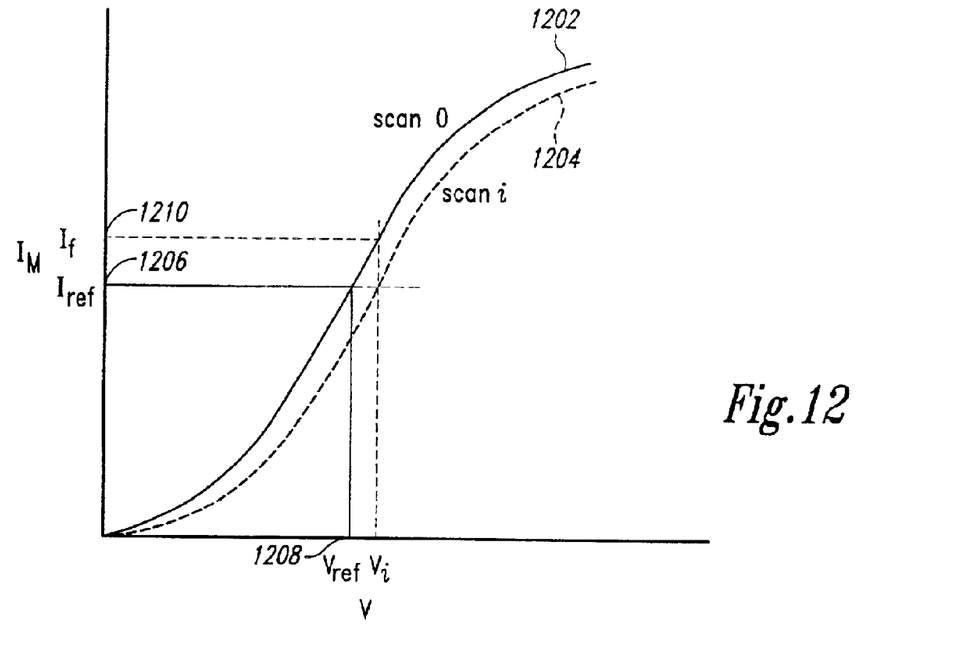
FIG. 12 illustrates the problem with using a same-dye reference array.

FIG. 12 illustrates the problem with using a same-dye array reference. The signal intensity deterioration over multiple scans, discussed above with reference to FIG. 11A, is reflected in FIG. 12 by different curves, or functional relationships, between output signal $I_m$, plotted along the vertical axis, and laser voltage, plotted along the horizontal axis. In this figure, and in subsequent figures and related discussion, it is assumed that the intensity of the coherent light emitted by a laser is a function of the voltage applied to the laser. The intensity of the laser light, as discussed above, may be adjusted using the attenuator components of the molecular array scanner, and can be adjusted in other ways. It is further assumed that the intensity of the laser light is adjusted in order to adjust the intensity of the output electronic signal from the molecular array scanner produced by illumination of a particular region of a reference array. As discussed, other components of the molecular array scanner, other than the laser-light intensity, may be adjusted in order to adjust the intensity of the output electronic signal from the molecular array scanner produced by illumination of a particular region of a reference array. Adjustment of voltage applied to the laser is employed in this discussion for simplicity of explanation, but is not intended to imply laser voltage adjustments as a preferred way to adjust output signal intensity.

In FIG. 12, curve 1202 corresponds to the relationship between voltage applied to the laser and the electronic signal generated by the molecular array scanner during the first scan, scan 0, of a same-dye reference array. The second curve 1204, plotted as a dashed curve, corresponds to the relationship between the voltage applied to the laser and the electronic signal generated by the molecular array scanner for the same region of the same-dye reference array on a subsequent scan, scan i, of the same-dye reference array. The scan i curve is displaced downward from the scan 0 curve due to degradation of the unstable dye molecular, as shown in FIG. 11A, above. During scan 0 of the same-dye reference array in the reference molecular array scanner, the reference molecular array scanner is internally calibrated to produce a signal intensity reference $I_{ref}$ 1206 corresponding to a laser voltage reference $V_{ref}$ 1208. When the same-dye reference array is used to calibrate a different molecular array scanner, the voltage applied to the laser of the different molecular array scanner, $V_i$, is adjusted in order to produce the same signal intensity $I_{ref}$ as produced by the reference molecular array scanner. However, because of the degradation of the dye, resulting in displacement of curve 1204 from curve 1202, the calibrated voltage $V_i$ is offset from $V_{ref}$. Thus, had the same-dye reference array been first scanned in the subsequently calibrated molecular array scanner at laser voltage $V_i$, the subsequently calibrated molecular array scanner would have produced an output signal intensity $I_f$ 1210 significantly larger than the output signal $I_{ref}$ produced by the reference molecular array scanner. In other words, the subsequently calibrated molecular array scanner has not been accurately calibrated to the reference molecular array scanner.

Figure 13:
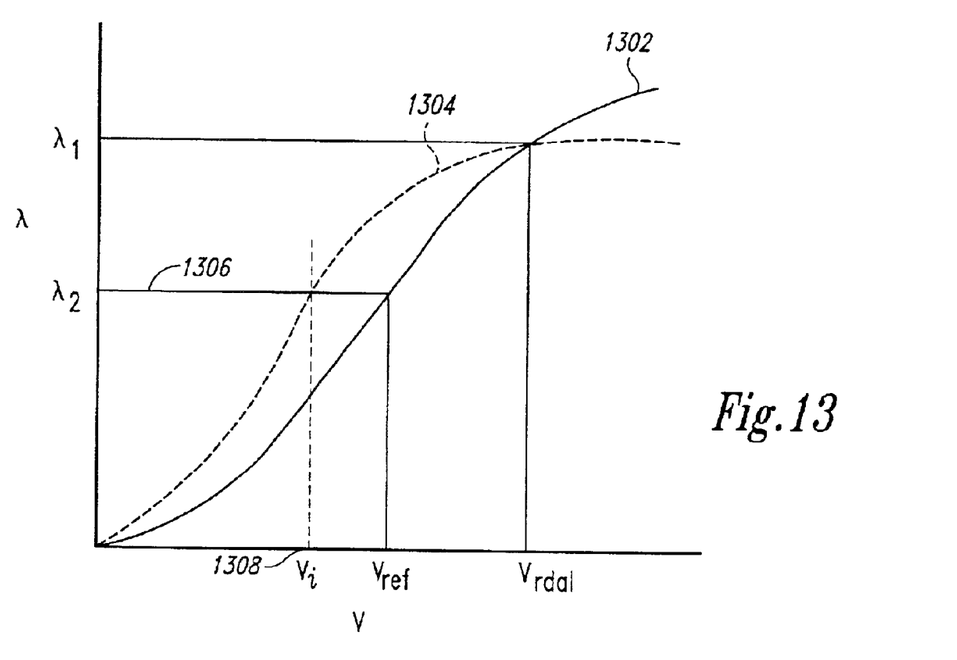
FIG. 13 illustrates a calibration problem inherent in stable-dye reference arrays.

FIG. 13 illustrates a calibration problem inherent in stable-dye reference arrays. The spectral response for the reference molecular array scanner 1302 and the spectral response for a subsequently calibrated molecular array scanner 1304 are both plotted in FIG. 13. In FIG. 13, the spectral response curves show a relationship between the wavelength of emitted light λ, plotted along the vertical axis, and the voltage applied to the laser, plotted along the horizontal axis, in order to produce a constant reference signal intensity $I_{ref}$. It may be the case, as shown in FIG. 13, that the voltage needed to be applied to the laser $V_{ideal}$ in order to generate signal intensity $I_{ref}$ at wavelength $\lambda_1$ emitted by the dye used to label probe molecules is the same for both the reference molecular array scanner and the subsequently calibrated molecular array scanner, as can be seen by the intersection of the two curves 1302 and 1304 at $V_{ideal}$ and $\lambda_1$. However, a stable dye may emit fluorescent light of a different wavelength than that of the dye actually used to label the probe molecules. If the reference molecular array scanner is internally calibrated to produce the output signal intensity $I_{ref}$ for stable-dye emission wavelength $\lambda_2$ at a voltage $V_{ref}$, as shown by the intersection of curve 1302 with the horizontal line corresponding to $\lambda_2$ 1306, then, due to a divergence in the spectral response of the reference molecular array scanner and the subsequently calibrated molecular array scanner, as seen in FIG. 13 by the lateral offset of the spectral response curve 1304 from the spectral response curve 1302, the voltage applied to the laser in the subsequently calibrated molecular array scanner $V_i$ 1308 is offset from the voltage applied to the laser of the reference molecular array scanner $V_{ref}$. Thus, due to the difference in the spectral response for the two molecular array scanners, calibration using the stable-dye reference array emitting fluorescent light at wavelength $\lambda_2$ results in a voltage difference $V_{ref}-V_i$ between the voltages applied to the lasers in the two molecular array scanners, although they would have been calibrated for the dye used to label probe molecules, emitting fluorescence at wavelength $\lambda_1$, by setting the laser voltages of both molecular array scanners to voltage $V_{ideal}$. Thus, as in the same-dye reference array calibration, the calibration method illustrated in FIG. 10, when used with a stable-dye reference array emitting fluorescent light at a different wavelength from that emitted by the dye compound used in probe molecules, results in an imprecise calibration of the two machines with respect to signal intensities produced by scanning molecular arrays with bound probe molecules labeled with an unstable dye compound.

Figure 14:
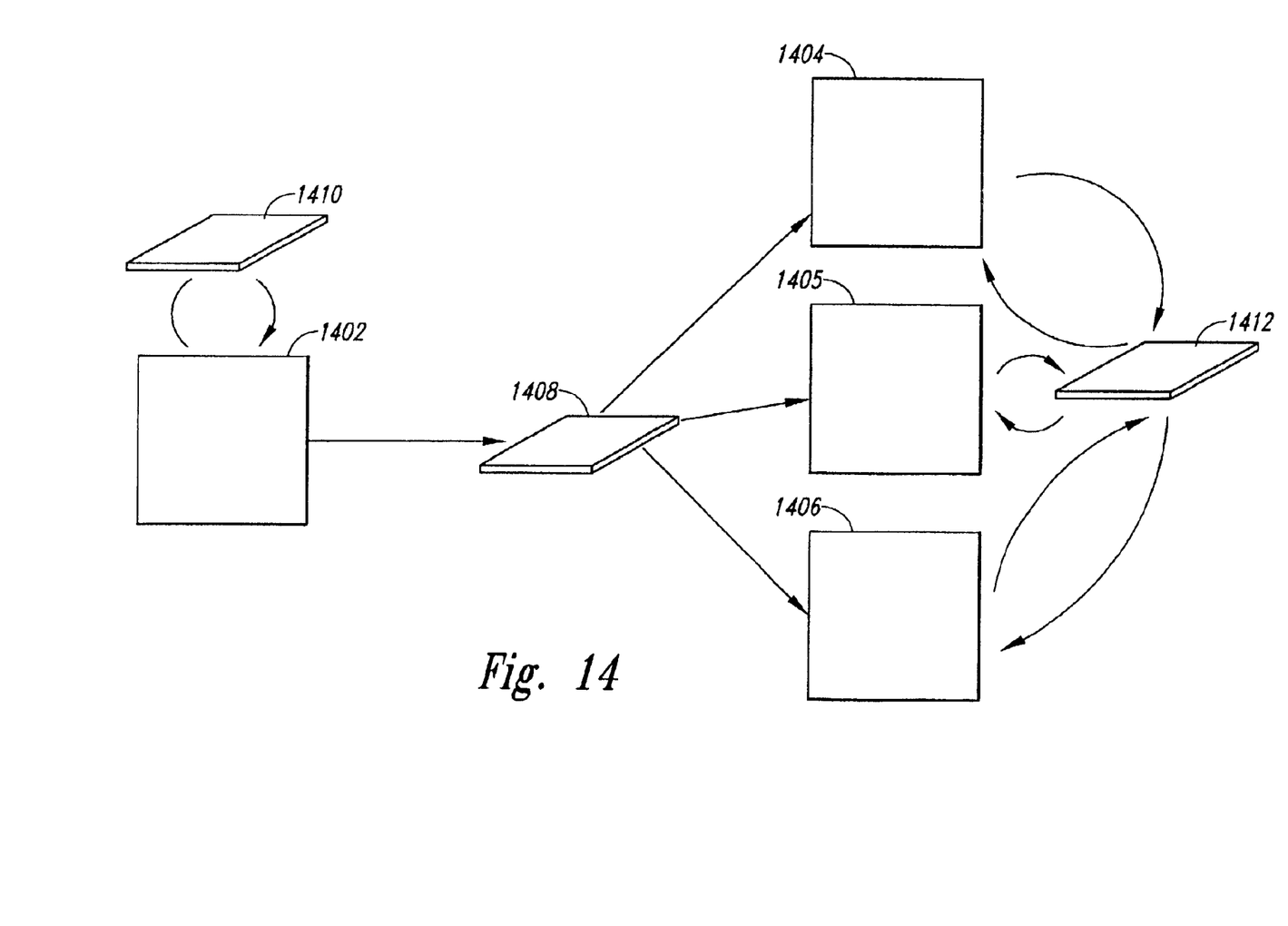
FIG. 14 illustrates the calibration method that represents one embodiment of the present invention.

In order to solve the same-dye reference array and stable-dye reference array problems, described above with reference to FIGS. 12 and 13, one embodiment of the present invention provides a different calibration method for calibrating molecular array scanners to a reference molecular array scanner. FIG. 14 illustrates the calibration method that represents one embodiment of the present invention. In FIG. 14, a reference molecular array scanner 1402 is used to calibrate a number of other molecular array scanners 1404–1406 so that all four molecular array scanners produce the same electronic output signal intensity when scanning a region of a molecular array containing a constant quantity of probe-molecule labels. The method that represents one embodiment of the present invention includes two steps. In the first step of the two-step method, a same-dye reference array 1408 is used, along with the pre-determined degradation characteristics of the same-dye molecular array, to calibrate the other molecular array scanners 1404–1406 to the reference molecular array scanner 1402. Then, the molecular array scanners are subsequently calibrated using one or more stable-dye reference arrays 1410 and 1412 to maintain the signal-intensity-to-dye-concentration ratio established during the first step of the two-step process.

Figure 15:
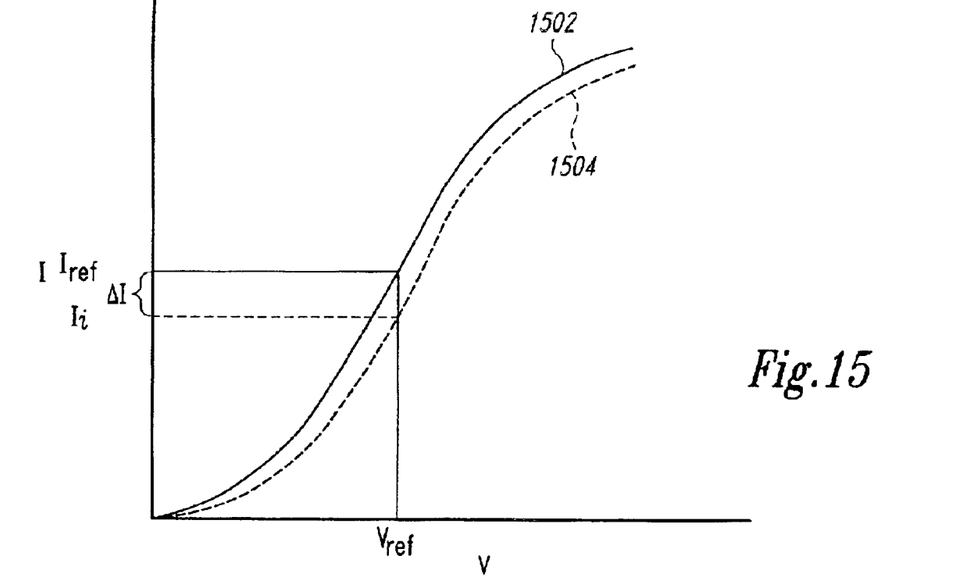
FIG. 15 illustrates the results of the first step of the two-step calibration method described with reference to FIG. 14.

FIG. 15 illustrates the results of the first step of the two-step calibration method described with reference to FIG. 14. In FIG. 15, the relationship between output signal intensity I, plotted along the vertical axis, and the voltage applied to the laser V, plotted along the horizontal axis, is shown for the first scan of the same-dye reference array (1408 in FIG. 14) as curve 1502, and the functional relationship between I and V for a subsequent scan of the same-dye reference array is shown as curve 1504. By using a known functional relationship between output signal intensity loss due to one scan of the same-dye reference array, an intensity differential $\Delta I$ can be calculated for the subsequent scan of the same-dye reference array. Thus, in calibrating a molecular array scanner, the appropriate $\Delta I$ is first calculated from a graph such as that shown in FIG. 11A, and then a desired reference signal intensity $I_i$ is calculated from the reference signal intensity $I_{ref}$ for the reference molecular array as: $I_i=I_{ref}-\Delta I$. Then, the voltage applied to the laser of the subsequently calibrated molecular array is adjusted to produce signal intensity $I_i$. Thus, the subsequently calibrated molecular array scanner has a laser voltage equal to the laser voltage that would be applied to the reference molecular array scanner in order to produce $I_{ref}$ during the first can of the same-dye reference array.

Figure 16:
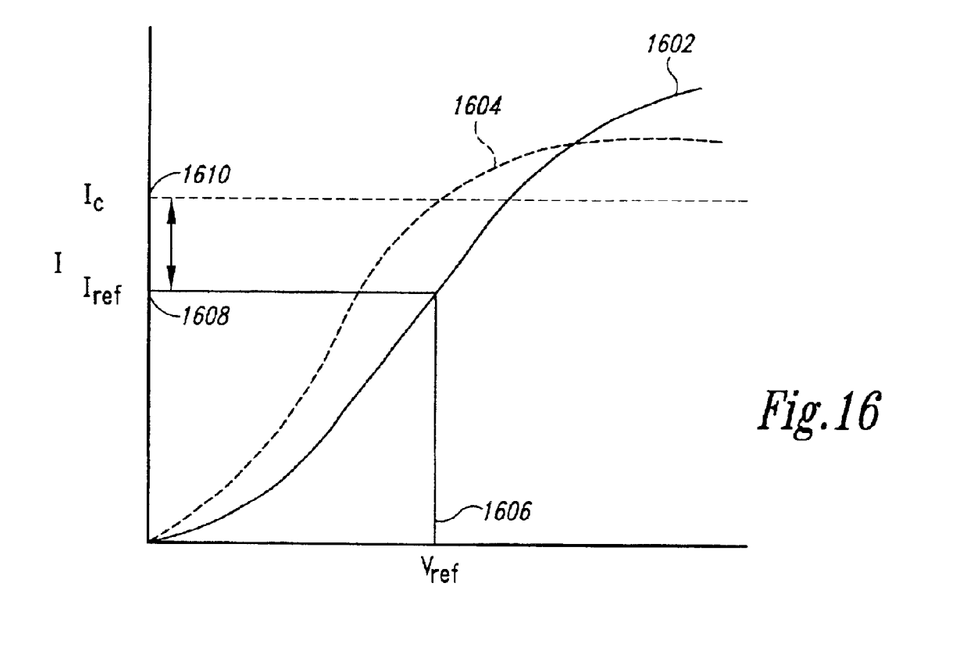
FIG. 16 illustrates the incremental calibration step of the two-step calibration method that represents one embodiment of the present invention.

FIG. 16 illustrates the subsequently applied calibration step of the two-step calibration method that represents one embodiment of the present invention. In FIG. 16, the functional relationships between the voltage applied to the laser, plotted along the horizontal axis, and the signal intensity output by the molecular array scanner I, plotted along the vertical axis, are shown for the actual dye used in the probe molecules 1602 and for the stable dye 1604 used in the stable-dye reference array. At a particular applied voltage $V_{ref}$ 1606, the dye used in probe molecules produces an output signal intensity $I_{ref}$ 1608, while the stable dye produces an output signal intensity $I_c$ 1610. Thus, assuming that the ratio $(I_c-I_{ref})/I_{ref}$ between the signal intensity output by the stable dye compared to the signal intensity output by the actual dye at a particular voltage remains constant, a molecular array scanner can be subsequently internally calibrated by adjusting the laser voltage to produce the output signal intensity $I^c$ when scanning a particular region of the stable-dye reference array.

Although the present invention has been described in terms of a particular embodiment, it is not intended that the invention be limited to this embodiment. Modifications within the spirit of the invention will be apparent to those skilled in the art. For example, scanning of reference arrays to produce integrated signals may be accomplished in many different ways. A constant scan pattern may be employed, and signal intensities associated with resulting pixels averaged or combined in more complex ways to produce an aggregate signal intensity. Alternatively, calibration may be iterated over a set of particular pixels. Calibration may be independently carried out for each signal channel using different reference arrays or a single reference array coated with a mixture of dye compounds responsive to the laser light of different wavelengths produced by the lasers within the molecular array scanner. Subsequent, internal calibrations can be carried out using a single stable-dye reference array, or using one stable-dye reference for each one, or for a set of, the molecular array scanners.

The foregoing description, for purposes of explanation, used specific nomenclature to provide a thorough understanding of the invention. However, it will be apparent to one skilled in the art that the specific details are not required in order to practice the invention. The foregoing descriptions of specific embodiments of the present invention are presented for purpose of illustration and description. They are not intended to be exhaustive or to limit the invention to the precise forms disclosed. Obviously many modifications and variations are possible in view of the above teachings. The embodiments are shown and described in order to best explain the principles of the invention and its practical applications, to thereby enable others skilled in the art to best utilize the invention and various embodiments with various modifications as are suited to the particular use contemplated. It is intended that the scope of the invention be defined by the following claims and their equivalents:

What is claimed is:

1. A method for calibrating a first molecular array scanner with a second, reference molecular array scanner, the method comprising:
    initially using a same-dye reference array comprising a first dye to calibrate the first molecular array scanner with the second, reference molecular array scanner; and
    maintaining the initial calibration of said first molecular array scanner with said reference molecular array scanner by scanning a stable-dye reference array comprising a second dye with the first molecular array scanner.

2. The method of claim 1 wherein said same-dye reference array is used to initially calibrate the first molecular array scanner with the second, reference molecular array scanner by:
    scanning the same-dye reference array in the second, reference molecular array scanner to determine a measured signal intensity for the same-dye reference array in the reference molecular array scanner;
    calculating an expected intensity for scanning the same-dye reference array in the second, reference molecular array scanner a second time; and
    scanning the same-dye reference array in the first scanner, and adjusting parameters in the first molecular array scanner to produce the expected intensity.

3. The method of claim 2 wherein calculating an expected intensity for scanning the same-dye reference array in the second, reference molecular array scanner a second time further comprises:
    determining a function of expected intensity per scan of the same-dye reference array; and
    selecting the expected intensity corresponding to one more than a number of times that the same-dye reference array has been scanned.

4. The method of claim 1 wherein maintaining the initial calibration further includes:
    following initial calibration, scanning a stable-dye reference array with the first molecular array scanner in order to determine a signal-intensity-to-stable-dye-concentration ratio; and
    periodically rescanning the stable-dye reference array with the first molecular array scanner, and adjusting the first molecular array scanner to provide the determined signal-intensity-to-stable-dye-concentration ratio.

5. A system for calibrating a number of molecular array scanners to provide a fixed signal-intensity-to-label-concentration ratio, the system comprising:
    a reference molecular array scanner;
    a number of molecular array scanners to be calibrated by the reference molecule array scanner
    a same-dye reference array comprising a first dye used to establish an initial calibration of each of the number of molecular array scanners to the reference molecular array scanner; and
    a stable-dye reference array comprising a second dye used to maintain the initiated calibration.

6. The system of claim 5 configured so that the same-dye reference array is used to establish an initial calibration of a first molecular array scanner to the reference molecular array scanner by:
    scanning the same-dye reference array in the reference molecular array scanner to determine a measured signal intensity for the same-dye reference array in the reference molecular array scanner;
    calculating an expected intensity for scanning the same-dye reference array in the reference molecular array scanner a second time; and
    adjusting the first molecular array scanner to produce the respective calculated expected intensity.

7. The system of claim 6 wherein calculating the expected intensity for scanning the same-dye reference array in the reference molecular array scanner a second time further comprises:
    determining a function of expected intensity per scan of the same-dye reference array; and
    selecting the expected intensity for the first molecular array scanner corresponding to one more than a number of times that the same-dye reference array has been scanned.

8. The system of claim 5 configured so that one or more stable-dye reference arrays are used to maintain the initial calibration of the first molecular array scanner by:
    initial calibration, scanning a stable-dye reference array with the first molecular array scanner in order to determine a signal-intensity-to-stable-dye-concentration ratio; and
    periodically rescanning the stable-dye reference array with the first molecular array scanner, and adjusting the first molecular array scanner to provide the determined signal-intensity-to-stable-dye-concentration ratio.

* * * * *